United States Patent
Telci et al.

(10) Patent No.: US 10,918,644 B2
(45) Date of Patent: Feb. 16, 2021

(54) CHEMOTHERAPEUTIC DRUG COMPOSITION

(71) Applicant: YEDITEPE UNIVERSITESI, Istanbul (TR)

(72) Inventors: Dilek Telci, Istanbul (TR); Ayse Hande Nayman, Istanbul (TR)

(73) Assignee: YEDITEPE UNIVERSITESI, Istanbul (TR)

( * ) Notice: Subject to any disclaimer, the term of this patent is extended or adjusted under 35 U.S.C. 154(b) by 0 days.

(21) Appl. No.: 16/490,085

(22) PCT Filed: Mar. 1, 2018

(86) PCT No.: PCT/TR2018/050073
§ 371 (c)(1),
(2) Date: Aug. 30, 2019

(87) PCT Pub. No.: WO2019/054966
PCT Pub. Date: Mar. 21, 2019

(65) Prior Publication Data
US 2020/0061075 A1    Feb. 27, 2020

(30) Foreign Application Priority Data
Mar. 1, 2017   (TR) ............... a 2017 03149

(51) Int. Cl.
*A61K 31/5377* (2006.01)
*A61P 35/00* (2006.01)
*A61K 31/436* (2006.01)

(52) U.S. Cl.
CPC ........ *A61K 31/5377* (2013.01); *A61K 31/436* (2013.01); *A61P 35/00* (2018.01)

(58) Field of Classification Search
CPC ............... A61K 31/436; A61K 31/635; A61K 31/5377; A61K 45/06; A61K 47/24; A61K 9/0019; A61K 2300/00; A61P 35/00
See application file for complete search history.

(56) References Cited

U.S. PATENT DOCUMENTS

| | | | |
|---|---|---|---|
| 2009/0098118 A1* | 4/2009 | Friess | A61P 43/00 424/133.1 |
| 2010/0280031 A1* | 11/2010 | David | A61K 31/5377 514/235.8 |
| 2011/0086025 A1* | 4/2011 | Friess | A61K 39/39533 424/133.1 |
| 2011/0159085 A1 | 6/2011 | Tong et al. | |
| 2012/0077837 A1* | 3/2012 | Okamoto | A61K 31/436 514/291 |
| 2016/0324878 A1 | 11/2016 | He | |
| 2017/0202782 A1* | 7/2017 | Pierce | A61K 9/0019 |
| 2018/0021259 A1* | 1/2018 | Heller | A61K 31/404 424/489 |

FOREIGN PATENT DOCUMENTS

| | | |
|---|---|---|
| KR | 20140074017 A | 6/2014 |
| WO | 2011133668 A | 10/2011 |

OTHER PUBLICATIONS

Selleckchem.com, ABT-737 data sheet, Nov. 22, 2012 (Year: 2012).*
Invivogen (https://www.invivogen.com/sites/default/files/invivogen/products/files/everolimus_tds.pdf product sheet, Everolimus, May 6, 2015). (Year: 2015).*
Cayman (ABT-263, product information, May 12, 2016) (Year: 2016).*
Jacques Ferlay et al. Estimates of Worldwide Burden of Cancer in 2008: GLOBOCAN 2008, International Journal of Cancer, 2010, 127, pp. 2893-2917.
Yasuhiro Yamamoto, et al. Treatment of Etoposide Combined with 15-deoxy-Δ12,14-prostaglandin J2 Exerted Synergistic Antitumor Effects against Renal Cell Carcinoma via Peroxisome Proliferator-activated Receptor-γ-Independent Pathway, Molecular and Clinical Oncology, 2014, 2, pp. 292-296.
Emiliano Calvo, et al. Contraversies in Renal Cell Carcinoma: Treatment Choice after Progression on Vascular Endothelial Growth-factor-targeted Therapy, European Journal of Cancer, 2014, 50 (7), pp. 1321-1329.
J.R. Gnarra, et al. Mutations of the VHL tumour Suppressor Gene in Renal Carcinoma, Nature Genetics, May 1994, 7(1), pp. 85-90.
Tatsuhiro Sato, et al. Characterization of the Rheb-mTOR Signaling Pathway in Mammalian Cells: Constitutive Active Mutants of Rheb and mTOR, Methods Enzymol., 2008, 438, pp. 307-320.
Gowrishankar Banumathy, et al. Signaling Pathways in Renal Cell Carcinoma, Cancer Biology& Therapy, Oct. 2010, 10(7), pp. 658-664.
Robert Motzer et al. Efficacy of Everolimus in Advanced Renal Cell Carcinoma: a Double-blind, Randomized, Placebo-controlled Phase III trial, Lancet, 2008, 372(9637), 449-456.

(Continued)

*Primary Examiner* — Umamaheswari Ramachandran
(74) *Attorney, Agent, or Firm* — Bayramoglu Law Offices LLC

(57) ABSTRACT

A chemotherapeutic drug composition, prepared by combination of Everolimus, one of the drugs used in the treatment of the metastatic renal cell carcinoma (RCC) comprising 2-3% of the malignant tumors, with the anti-apoptotic Bcl-2 inhibitor ABT-737 for the treatment of RCC tumors that developed drug resistance. The effect of Everolimus and ABT-737 drug composition on cell survival and cell death in Everolimus-resistant RCC cell lines overexpressing Bcl-2 protein was shown by in vitro and in vivo experiments and the mechanism of the effect of the drug composition on RCC has been examined from a molecular point of view. Navitoclax (ABT-263), an orally available analog of ABT-737, and other Bcl-2 inhibitors alone or in combination with Everolimus, which is administered once a day at a dose of 10 mg, for the use in the treatment of Everolimus-resistant RCC.

3 Claims, 10 Drawing Sheets

(56) References Cited

OTHER PUBLICATIONS

Eva Juengel, et al. Combining the Receptor Tyrosine Kinase Inhibitor AEE788 and the Mammalian Target of Rapamycin (mTOR) Inhibitor RAD001 Strongly Inhibits Adhesion and Growth of Renal Cell Carcinoma Cells, BMC Cancer, May 2009, 9, 161.
Eric J. Brown, et al. A Mammalian Protein Targeted by G1-arresting Rapamycin-receptor Complex, Nature, 1994, 369, pp. 756-758.
Won Jun Oh, et al. mTOR Complex 2 Signaling and Functions, Cell Cycle, Jul. 2011, 10(14), pp. 2305-2316.
Mathieu Laplante, et al. mTOR Signaling in Growth Control and Disease, Cell, Apr. 2013, 149 (2), pp. 274-293.
Matteo Santoni, et al. Emerging Strategies to Overcome the Resistance to Current mTOR Inhibitors in Renal Cell Carcinoma, Biochimica et Biophysica Acta., 2014, 1845(2), pp. 221-231.
Suzanne Cory, et al. Killing Cancer Cells by Flipping the Bcl-2/Bax Switch, Cancer Cell, Jul. 2005, 8(1), pp. 5-6.
Naval Bajwa, et al. Inhibitors of the Anti-apoptotic Bcl-2 Proteins: a Patent Review, Expert Opin Ther Pat. Jan. 2013, 22(1), pp. 37-55.
JM Adams, et al. The Bcl-2 Apoptotic Switch in Cancer Development and Therapy, Oncogene, Feb. 2007, 26(9), pp. 1324-1337.
Asfar S. Azmi et al. Non-peptidic Small Molecule Inhibitors against Bcl-2 for Cancer Therapy, J Cell Physiol., Jan. 2009, 218(1),pp. 13-21.
V Labi, et al. Targeting the Bcl-2-regulated Apoptosis Pathway by BH3 Mimetics: a Breakthrough in Anticancer Therapy?, Cell Death Differ., Jun. 2008, 15(6), pp. 977-987.
Steven W. Muchmore, et al. X-ray and NMR Structure of Human Bcl-xL, an Inhibitor of Programmed Cell Death, Nature, May 1996, 381(6580), pp. 335-341.
Suzanne Cory et al. The Bcl2 Family: Regulators of the Cellular Life-or-Death Switch, Nat Rev Cancer, Sep. 2002, 2(9), pp. 647-656.
Marina Konopleva, et al. Mechanisms of Apoptosis Sensitivity and Resistance to the BH3 Mimetic ABT-737 in Acute Myeloid Leukemia, Cancer Cell, Nov. 2006, 10, pp. 375-388.
Maurizio Pellecchia et al. Inhibition of Anti-apoptotic Bcl-2 Family Proteins by Natural Polyphenols: New Avenues for Cancer Chemoprevention and Chemotherapy, Curr Pharm Des., 2004, 10(12), pp. 1387-1398.
M Vogler et al. Bcl-2 Inhibitors: Small Molecules with a Big Impact on Cancer Therapy, Cell Death Differ., 2009,16 (3), pp. 360-367.
Yoshiniko Tomita et al. Frequent Expression of Bcl-2 in Renal-cell Carcinomas Carrying Wild-type p53, Int J Cancer. 1996, 66, pp. 322-325.
Lin Zheng, et al. GDC-0941 Sensitizes Breast Cancer to ABT-737 in Vitro and in Vivo through Promoting the Degradation of Mcl-1, Cancer Lett., 2011, 309(1), pp. 27-36.
Henry Zall, et al. Chemotherapeutic Drugs Sensitize Human Renal Cell Carcinoma Cells to ABT-737 by a Mechanism involving the Noxa-dependent Inactivation of Mcl-1 or A1, Mol Cancer,2010, 9, 164.
Christin Tse, et al. ABT-263: a Potent and Orally Bioavailable Bcl-2 Family Inhibitor, Cancer Research, 2008, vol. 68, No. 9, pp. 3421-3428.
Wyndham H Wilson, et al. Navito-clax, a Targeted High-Affinity Inhibitor of BCL-2, in Lym-phoid Malignancies: a Phase 1 Dose-escalation Study of Safety, Pharmacokinetics, Pharmacodynamics, and Antitu-mour Activity. Lancet Oncol., Dec. 2010, 11, pp. 1149-1159.
Andrew W. Roberts, et al. Substantial Susceptibility of Chronic Lymphocytic Leukemia to BCL2 Inhibition: Results of a Phase I Study of Navitoclax in Patients with Relapsed or Refractory Disease, J Clin Oncol., Feb. 2012, 30, pp. 488-496.
Leena Gandhi, et al. Phase I Study of Navitoclax (ABT-263), a Novel bcl-2 Family Inhibitor, in Patients with Small-cell Lung Cancer and Other Solid Tumors, Journal of Clinical Oncology, Mar. 2011, 29, pp. 909-916.
Charles M. Rudin, et al. Phase II Study of Single-agent Navitoclax (ABT-263) and Biomarker Correlates in Patients with Relapsed Small Cell Lung Cancer, Clinical Cancer Research, Jun. 2012, vol. 18, No. 11, pp. 3163-3169.
Kiran Gupta, et al. Epidemiologic and Socioeconomic Burden of Metastatic Renal Cell Carcinoma (mRCC): a Literature Review. Cancer Treat Rev, 2008, 34(3), pp. 193-205.
Borje Ljungberg et al. European Association of Urology Guideline Group. EAU guidelines on renal cell carcinoma: the 2010 update, Eur Urol.,2010, 58(3), pp. 398-406.
Bernard Escudier, et al. Sorafenib in Advanced Clear-cell Renal-cell Carcinoma, N Engl J Med., Jan. 2007, 356 (2), pp. 125-134.
G.P. Murphy, et al. A Murine Renal Cell Carcinoma, J Natl Cancer Inst., Apr. 1973, 50(4), pp. 1013-1025.
M. Rosner, et al. Evidence for Cell Cycle-dependent, Rapamycin-resistant Phosphorylation of Ribosomal Protein S6 at S240/244, Amino Acids, 2010, 39, pp. 1487-1492.
Luca Scorrano et al. Mechanisms of Cytochrome c Release by Proapoptotic BCL-2 Family Members, Biochem Biophys Res Commun., 2003, 304(3), pp. 437-444.
Shawn B. Bratton, et al. Regulation of the Apaf-1-caspase-9 Apoptosome, J Cell Sci., 2010, 123(Pt 19), pp. 3209-3214.
Dongzhu Ma, et al. Rheb GTPase Controls Apoptosis by Regulating Interaction of FKBP38 with Bcl-2 and Bcl-XL, J Biol Chem, Mar. 2010, 285(12), pp. 8621-8627.
Marina K. Holz, et al. mTOR and S6K1 Mediate Assembly of the Translation Preinitiation Complex through Dynamic Protein Interchange and Ordered Phosphorylation Events, Cell, Nov. 2005, 123, pp. 569-580.

\* cited by examiner

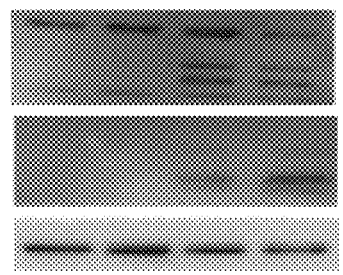
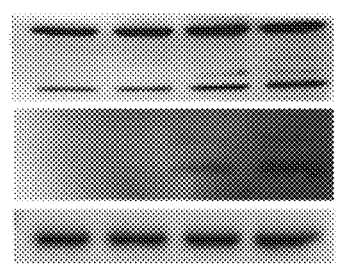
Fig. 9a
Fig. 9b
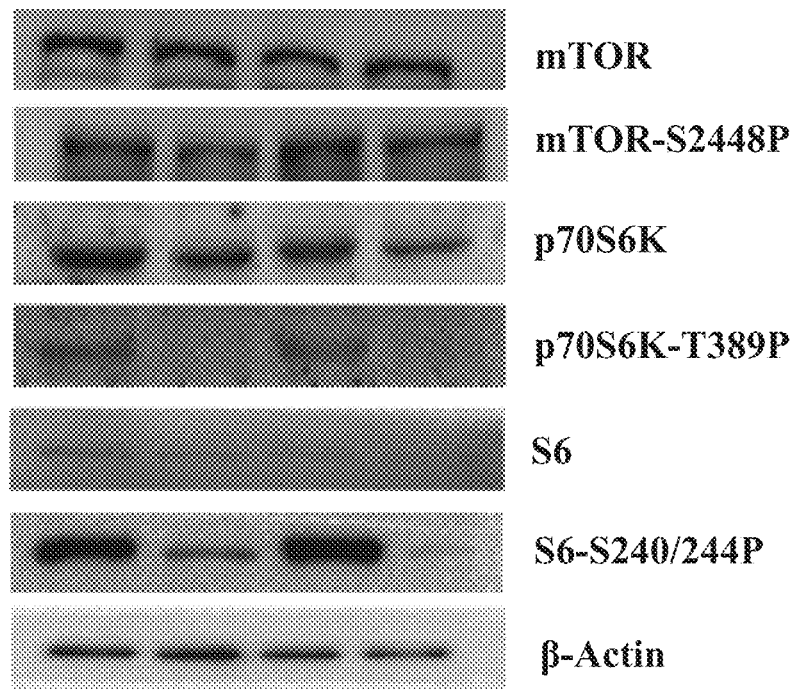
Fig. 10

CHEMOTHERAPEUTIC DRUG COMPOSITION

CROSS REFERENCE TO THE RELATED APPLICATIONS

This application is the national phase entry of International Application No. PCT/TR 2018/050073, filed on Mar. 1, 2018, which is based upon and claims priority from the Turkish Patent Application No. 2017/03149, filed on Mar. 1, 2017, the entire contents of which are incorporated herein by reference.

TECHNICAL FIELD

The present invention relates to a chemotherapeutic drug composition comprising ABT-737 and/or ABT-737 analog Navitoclax (ABT-263) with Everolimus solution and/or other mTOR pathway inhibitor rapalog(s) for the use in treatment of kidney cancer.

BACKGROUND

According to 2009 data of Cancer Department of Turkish Public Health Agency, 20.7% of deaths are due to cancer. 5.1% of the cancers encountered in men comprise kidney cancers. In the European Union countries, the incidence of kidney cancer is calculated to be 15.8 per 100,000 in men and 7.1 per 100,000 in women. The same data reveal that mortality rate is 6.5 per 100.000 in men and 2.7 per 100.000 in women. In adults, the most prevalent cancer observed in kidneys is renal cell carcinoma (RCC). Due to the fact that RCC is resistant to radiotherapy and chemotherapy, 5-year survival of metastatic RCC is under 10%. Today, there are 7 licensed drugs approved for the treatment of metastatic RCC. These are Bevacizumab (anti-endothelial growth factor monoclonal antibody, used in combination with interferon); tyrosine kinase inhibitors Sunitinib, Pazopanib, Axitinib, Sorafenib; and mTOR (mammalian target of rapamycin) inhibitors Everolimus (RAD001) and Temsirolimus.

The mutations causing to the development of kidney cancer are frequently observed in the gene encoding the von Hippel-Lindau (VHL) tumor suppressor protein. The presence of mutation in the VHL gene observed in 90% of the RCC tumors causes these tumors to mimic the hypoxic environmental conditions resulting in intensive vascularization, rapid growth, and high invasive potential. It has been reported that HIF-α (hypoxia-induced factor-α) transcription factors activated by VHL dysfunction activate the PI3K (phosphotidylinositol-3-kinase)-AKT-mTOR survival pathway and cause to accumulation of mutation that enables cell transformation. mTOR (mammalian target of rapamycin complex) pathway is an intracellular signaling pathway located in the PI3K-AKT-mTOR axis. The pathway is induced by growth factors and is in the center of the important cellular processes such as cell growth, proliferation, migration, survival, and angiogenesis. Considering the important roles of mTOR pathways in cell survival/growth as well as stimulation of protein synthesis, the above mentioned rapamycin or other rapamycin analogs (Rapalog) such as Everolimus and Temsirolimus are used as chemotherapeutic agents for the inhibition of the mTOR pathway in mTOR pathway-dependent RCC, ovarian and bone cancer treatments.

The use of these drugs in the treatment of metastatic RCC is intended to inhibit cell growth/survival by blocking the mTOR kinase pathway. Although 7 drugs mentioned above are used for the treatment of metastatic RCC, the resistance develops against these drugs in all patients and some patients cannot even take these drugs due to their side effects. In the clinical studies conducted so far, progression-free survival has been considered as the first outcome point and it ranges from 1.1 months to 8.3 months. In fact, in advanced stage RCC treatment, Everolimus received FDA (U.S. Food and Drug Administration) approval in 2009 after failure of VEGF therapy and it increased the survival only about 4.9 months in Phase III clinical trials. Nevertheless, an overall survival advantage was not observed. Furthermore, it was observed in the in vitro experiments that rapalog treatment decreased the cell growth by 33%-57% in Caki-1, KTC-26 and A-498 RCC cell lines, but it did not lead to cell death.

Rapalogs (Everolimus, Temsirolimus and Deferolimus) bind to the 12 kilodalton cytoplasmic protein FKBP12 and only inhibit mTOR kinase in the mTORC1 complex. Although Rapalog derivatives are efficient in the beginning of cancer treatment, they lose their effect in the later stages of the treatment process as the tumors develop resistance against these drugs.

Although the activity of mTORC2 is shown to be the cause for the development of resistance against these drugs, it has been reported in the following studies that a prolonged rapalog therapy can also inhibit the mTORC2 complex and the AKT signaling pathways dependent on this complex. This can be explained by re-activation of PI3K, MAPK (mitogen-activated protein kinase) and IGF (insulin-like growth factor) feedback pathways, which are inhibited by mTORC1 in rapalog-resistant tumors.

Accordingly, many studies in the literature have shown that the expression level of anti-apoptotic Bcl-2 protein increases in cancer cells and that this increase causes to the development of resistance to chemotherapy and radiotherapy. For this reason, drugs such as TW-37, obatoclax, ABT-737 targeting anti-apoptotic Bcl-2 protein were developed and commercialized. The purpose of these drugs is to bind to the BH3 domain of the Bcl-2 proteins thereby preventing them from interacting with pro-apoptotic proteins. In other words, these inhibitor drugs, which bind to the hydrophobic groove formed by the BH3 domain of the anti-apoptotic Bcl-2 protein family members, prevent the inactivation of the pro-apoptotic proteins mediated by Bcl-2 anti-apoptotic proteins. ABT-737 is a Bcl-2 inhibitor developed by Abbott Laboratories and it binds to the BH3 domain of the anti-apoptotic proteins Bcl-2, Bcl-xL and Bcl-w thereby preventing the binding of pro-apoptotic proteins to this domain. The fact that the increase in expression of anti-apoptotic Bcl-2 protein observed in RCC cell lines is in parallel with the development of drug resistance suggests that ABT-737, which has been used in various studies reported in the literature, can also be tested on these cells. For example, a study showed that the use of the drug combination of ABT-737 and Taxol group on RCC cell lines such as RCC-21, RCC-26A, RCC-30, Caci-2 reduced the resistance of these cells to Taxol-induced apoptosis. Moreover, ABT-737 has been tested and proven successful in preclinical experiments performed in lymphoma, multiple myeloma, breast cancer, small cell lung cancer, squamous cell head and neck cancer, and various leukemia cancer models. However, there are no preclinical or in vitro studies wherein ABT-737 is used for the treatment of RCC. The ABT-737 analog ABT-263 was developed for the oral solubility and used as the ABT-737 agent in the transition from preclinical studies to clinical studies. Clinical trials of the orally administered ABT-263 were tested on lymphatic malignant tumors and solid tumor types. ABT-263, which is used by the name Navitoclax in clinical trials, has been used in phase 1 trials for patients with small cell lung cancer (SCLC) and in phase two trials for patients with relapsed SCLC and chemotherapy-resistant SCLC. As a result of these clinical phase studies, the effect of Navitoclax as a monotherapy agent in the treatment was determined to be limited and it was recommended to be used in combination treatments. In the light of these experiments in the literature, it was aimed in the study of the present patent application to use ABT-737 agent having the function of Navitoclax Bcl-2 inhibitor in the treatment of RCC that is resistant to Everolimus or other rapalog drugs.

Renal cell carcinoma (RCC) accounts for 2-3% of the malignant tumors in adults. The fact that 102,000 people out of 200,000 people diagnosed with kidney cancer each year lose their lives shows that mortality rate of RCC is about 50%. Renal cell carcinoma is one of the most common (90%) malignant tumors among the cancer types of kidney. The most commonly used method in the treatment of RCC is the removal of the localized cancer from the kidney by radical or partial nephrectomy. The incidence of the postoperative recurrence is high in RCC and the cancer is usually diagnosed at the metastatic stage. As RCC diagnosed at the metastatic stage is resistant to radiotherapy and chemotherapy, 5-year survival is below 10%. The identification of the molecular mechanism, which plays a role in the development of RCC and in the resistance to radiotherapy and chemotherapy observed in metastatic RCC, has brought up the targeted drug treatment. Interleukin-alpha and interleukin-2 based cytokines are the first drugs used under the name of targeted drug treatment. Inefficiency of the cytokines used in the treatment and their several side effects have limited the treatment of metastatic RCC to 7 licensed drugs at the present time. These are Bevacizumab (anti-endothelial growth factor monoclonal antibody, used in combination with interferon); tyrosine kinase inhibitors Sunitinib, Pazopanib, Axitinib, Sorafenib; and mTOR (mammalian target of rapamycin) inhibitors Everolimus and Temsirolimus. Sorafenib, which is one of the tyrosine kinase inhibitors used in first-line treatment, prolongs the progression-free survival up to 5.9 months. Temsirolimus, which is one of the mTOR inhibitors used in second-line treatment, prolongs the survival up to 3.8 months, whereas prolonged progression-free survival up to 4.9 months was reported for the Everolimus treatment.

Korean patent document no. KR20140074017 discloses the use of a combination of cafestol, which is a diterpene compound in coffee, and ABT-737 Bcl-2 protein inhibitor for the treatment of kidney cancer.

SUMMARY

The objective of the present invention is to provide a chemotherapeutic drug composition, which can be actively used in RCC treatment and will make a difference in overall survival.

Another objective of the present invention is to demonstrate the success of the combined therapy with anti-apoptotic Bcl-2 inhibitor ABT-737 in RCC tumors that developed Rapalog (Everolimus, Temsirolimus and Deferolimus) drug resistance for the RCC treatment.

A further objective of the present invention is to provide a chemotherapeutic drug composition which can be easily prepared and which provides a definitive and rapid treatment in RCC treatment.

Another objective of the present invention is to provide a chemotherapeutic drug composition that induces the cell death in rapalog-resistant tumors that possess anti-apoptotic Bcl-2 protein activation.

BRIEF DESCRIPTION OF THE DRAWINGS

"Chemotherapeutic drug composition" carried out to fulfill the objectives of the present invention is illustrated in the accompanying figures, in which:

FIGS. 9A-9B show the effect of the drug composition on the molecular mechanism playing a role in the cell death for (a) A-498 and (b) Caki-1 cells.

FIG. 10 demonstrates the effect of the drug composition on mTOR pathway for A-498 cells. mTOR: Mammalian target of rapamycin; mTOR-S2448P: a phosphorylated derivate of Mammalian target of rapamycin at serine 2448 site; p70S6K: Ribosomal protein S6 kinase; p70S6K-T389P: a phosphorylated derivate of Ribosomal protein S6 kinase in threonin 389 region; S6: Ribosomal protein; S6, S6-S240/244P: phosphorylated derivate of Ribosomal protein S6 at serine 240/244 site. Cytoskeleton protein β-Actin was used to show equal loading.

DETAILED DESCRIPTION OF THE EMBODIMENTS

Within the scope of the invention, a chemotherapeutic drug composition composed of ABT-737 and/or Navitoclax (ABT-263) solution, the orally administered analog of ABT-737, is used in the treatment of Rapalog-resistant advanced stage kidney cancer and kidney cancer originated from renal cell carcinoma (RCC). The application of the invention is using the solution of ABT-737 and/or Navitoclax (ABT-263), the orally administered analog of ABT-737 together with, the solution of Everolimus for the treatment of rapalog-resistant renal cell cancer.

The method of preparing the solution of ABT-737 and/or Navitoclax (ABT-263), the ABT-737 analog, present in the chemotherapeutic drug composition that is the scope of the present invention comprises the steps of
preparing a ABT-737 and/or Navitoclax (ABT-263), which is an orally available analog of ABT-737 stock solution with a concentration of 10 mM by dissolving 10 mg ABT-737 and/or Navitoclax (ABT-263 in 1.229 ml DMSO (8.14 mg/ml),
for in vivo conditions, diluting the sample taken from the stock concentration of ABT-737 and/or Navitoclax (ABT-263), which is an orally available analog of ABT-737, in PBS (Phosphate-buffered saline) to have the drug concentration of 75 mg/kg,
preparing the solution of ABT-737 and/or Navitoclax (ABT-263), which is an orally available analog of ABT-737.

The method of preparing the Everolimus solution present in the chemotherapeutic drug composition that is the scope of the present invention comprises the steps of
preparing Everolimus stock solution with a concentration of 10 mM by dissolving 10 mg lyophilized Everolimus in 1.043 ml DMSO (Dimethyl sulfoxide) (9.6 mg/ml),
for in vivo conditions, diluting the sample taken from Everolimus stock concentration in PBS (Phosphate-buffered saline) to have the drug concentration of 2 mg/kg,
preparing the Everolimus solution.

Figure 1:
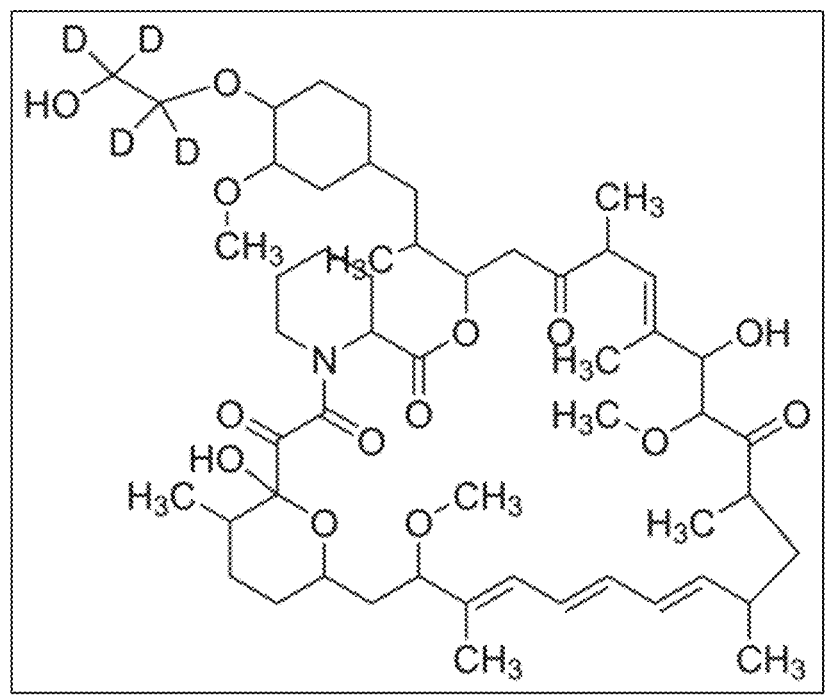
FIG. 1 is a representation of the chemical structure of Everolimus.
Figure 2:
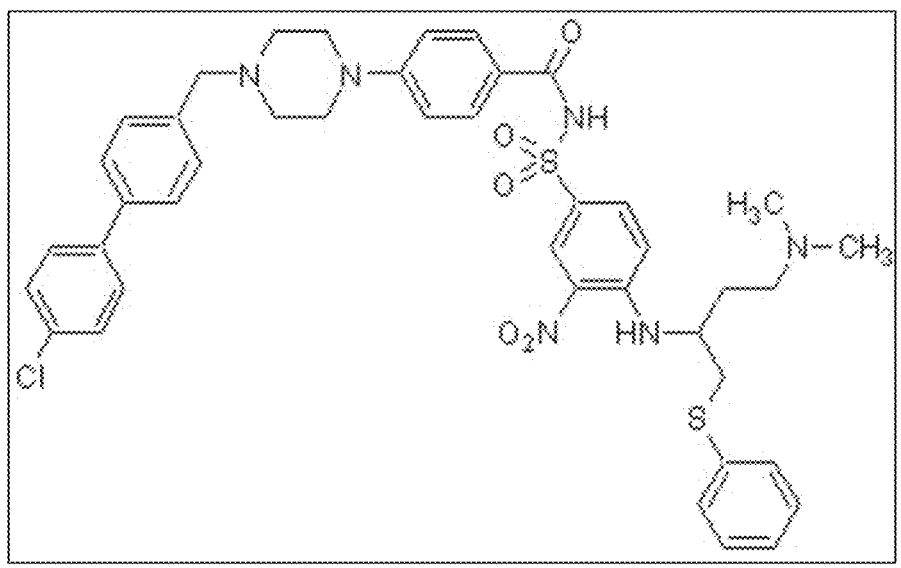
FIG. 2 is a representation of the chemical structure of ABT-737.

Bcl-2 protein levels were measured in A-498, Caki-2, Caki-1 and ACHN cell lines, which are commonly used as renal cell carcinoma (RCC) cell models and two cell lines (A-498 and Caki-1) overexpressing Bcl-2 protein were determined. These cell lines were identified as being resistant to Everolimus therapeutic agent whose formula is shown in FIG. 1. Cell viability assays and cell death assays were used to determine Everolimus resistance. These cells were treated with various doses of ABT-737 to determine the effect of ABT-737 (FIG. 2) agent to overcome Everolimus resistance. The minimum effective concentration of ABT-737 was combined with Everolimus and used on A-498 and Caki-1 cells.

It has been found in the cell viability and apoptosis measurement assays that ABT-737/Everolimus combination therapy is more effective than monotherapy with either of the drugs. In order to transfer the results obtained in in vitro experiments to the animal model and to complete the preclinical phase of the study; RenCa cells, which overexpress Bcl-2 protein, were made resistant to the drug Everolimus, and these cells were named as erRenCa. Mono- and combination therapies were initiated within 4 days following transplantation of these Everolimus-resistant RCC RenCa cells into the dorsal area of the animals. Tumor formation was observed in animals in the control group not receiving any treatment and in animals receiving monotherapy, whereas no tumor formation was observed in animals receiving combination therapy. Following termination of the study, pathological examination of the tissues revealed that mono- and combination therapies did not show any toxic effects on the animals. It was found that combination therapy completely suppressed tumor formation while monotherapy with Everolimus and ABT-737 could not inhibit tumor formation in the animals.

Experimental Study
Preparing the Drug Composition

Everolimus and ABT-737 drug composition prepared for the treatment of renal cell carcinoma (RCC) was prepared in different concentrations for in vitro and in vivo conditions and applied in the experiments.

During Preparation of the Drug Composition,

Everolimus stock solution was prepared by dissolving 10 mg lyophilized Everolimus in 1.043 ml DMSO (Dimethyl sulfoxide) (9.6 mg/ml) and ABT-737 stock solution was prepared by dissolving 10 mg ABT-737 in 1.229 ml DMSO (8.14 mg/ml). Stock concentration of both drugs was 10 mM. For in vitro conditions, dilutions were made in cell culture medium at concentrations ranging from 1-5 µM from Everolimus stock concentration. For in vivo conditions, the drug Everolimus that will be injected to animals was prepared by diluting the stock concentration in PBS (Phosphate-buffered saline) to a concentration of 2 mg/kg. For in vitro conditions, dilutions were made in cell culture medium at concentrations ranging from 1-10 µM from ABT-737 stock concentration. For in vivo conditions, the drug ABT-737 that will be injected to animals was prepared by diluting the stock concentration in PBS (Phosphate-buffered saline) to a concentration of 75 mg/kg. Prior to injection, the volume of the injected drug is adjusted to 200 µl by addition of PBS (Phosphate-buffered saline). The drugs were injected into the animals separately one minute apart without being mixed.

Determining Cell Toxicity

The WST-1 assay was performed to determine cell viability. The working principle of this assay is based on the conversion of the stable tetrazolium salt WST-1 into soluble formazan by viable cells. During conversion of WST-1 to formazan, a color change that is measurable at 450 and 630 nm wavelengths occurs in the cell medium. In other words, the amount of formazan dye is proportional to the number of metabolically active (viable) cells. The color change was evaluated by measuring the absorbance in the ELISA device and the obtained values were analyzed using the Graph Pad Prism 7 database.

To determine the toxic effect of Everolimus and ABT-737 on cell viability, primary A-498 and metastatic Caki-1 RCC cell lines that are resistant to drug Everolimus were used in this study and the toxic effect was determined by using the WST-1 method.

Everolimus and ABT-737 drugs were administered to A-498 and Caki-1 cells, which were seeded in 96-well culture plates, for three days to determine the appropriate dose for the combination. The effect of the drugs prepared at three different concentrations (1, 5, or 10 µM) on cell viability was determined using the WST-1 method. As a result of this experiment, the drug composition was prepared at concentrations of 1 µM for Everolimus and 5 µM for ABT-737 and it was tested on A-498 cells seeded in 96-well culture plates (2000 cells/well). The amount of drug composition for Caki-1 (10,000 cells/well) metastatic cells was determined as 1 μM Everolimus and 10 μM ABT-737. The response of the cells to the drug composition was determined by measuring the cell viability for 3 days.

Human embryonic kidney (HEK293) cells were used as a cell model to test whether Everolimus and ABT-737 had any toxic effects on healthy kidney cells. HEK293 cells were treated with the drug composition (1 μM for Everolimus and 5 μM for ABT-737) for 3 days and the toxicity response was determined by measuring cell viability by WST-1 assay for 3 days.

Determining Cell Death

Annexin-V cell death detection assay was used to test whether the decrease in cell viability observed during the toxicology analysis depends on the cell death. 1 μM Everolimus and 5 μM ABT-737 were prepared for A-498 RCC cells and 1 μM Everolimus and 10 μM ABT-737 were prepared for Caki-1 RCC cells and they were applied to the cells grown in 6-well culture plates for 3 days. Annexin-V method was performed at the end of 24, 48 and 72 hours and the analyses were done using Microsoft Excel database.

Determination of the Effect of the Drug Composition on Apoptosis Molecular Mechanism To investigate the effect of the drug composition on the molecular mechanism of the cell death, A-498 cells and Caki-1 cells seeded in 6-well plates were treated for 24 hours with 1 μM Everolimus and 5 μM ABT-737, and 1 μM Everolimus and 10 μM ABT-737, respectively. At the end of 24 hours, expression of caspase proteins was determined in the protein lysates by using Western Blotting technique.

Determination of the Effect of the Drug Composition on mTOR Pathway

A-498 and Caki-1 RCC cells were used to investigate the molecular effect of the Everolimus and ABT-737 drug composition on the mTOR pathway. A-498 cells and Caki-1 cells seeded in 6-well plates were treated for 24 hours with 1 μM Everolimus and 5 μM ABT-737 and 1 μM Everolimus and 10 μM ABT-737, respectively. At the end of 24 hours, proteins were isolated from the cells. These proteins were then used to determine the expression of proteins that play a key role in the mTOR pathway by performing the Western Blotting technique.

Generation of Everolimus-Resistant RenCa Cells

RenCa cells were made resistant to Everolimus for the use in in vivo experiments. In this regard, RenCa cells were seeded in 96-well culture plates. After 24 hours, the cells were treated with 1 μM Everolimus for 72 hours. At the end of 72 hours, the cells were washed with PBS (Phosphate-buffered saline) and treated with 10 μM Everolimus for an additional 72 hours. Cells that developed resistance to Everolimus were transferred to 6-well culture plates and were grown in an Everolimus-free medium. Cells reaching a density of 90% were transferred to T-75 culture plates and were grown for 2 months in a medium containing 1 μM Everolimus.

Generation of erRenCa Cells and In Vivo Tumor Model

Regarding to identification that Everolimus and ABT-737 drug composition causes cell death in A-498 and Caki-1 RCC cell lines in in vitro conditions, RenCa cells were used to investigate whether the composition had the same effect in in vivo conditions. RenCa cells were first treated for three days with Everolimus prepared at different concentrations (1, 5, and 10 μM). The results obtained with the WST-1 cell viability assay showed that RenCa cells were sensitive to Everolimus. Therefore, RenCa cells were made resistant to Everolimus in order to transfer the Everolimus-resistant RCC cell model to the animal model. In this regard, RenCa cells were grown in a medium containing Everolimus for 2 months. WST-1 cell viability assay was used to determine whether the cells acquired resistance to the drug. The development of the tumor tissue was performed by the implantation of RenCa cells, which were made resistant to Everolimus, into the dorsal area of the animals [34, 35]. The process of tumor development was monitored. At the end of a period of about 10 days, the tumors grew to visible sizes. In order to investigate the effects of the drug composition on tumor formation, drug therapy was initiated at the fourth day after tumor implantation. Four groups of animals were used in our experimental setup. The solutions, in which the drugs were dissolved, were administered to the 8 animals in the 1st group by intraperitoneal injection every other day after tumor implantation. 2 mg/kg Everolimus was administered to the animals in Group 2 by intraperitoneal injection every other day, whereas 75 mg/kg ABT-737 was administered to the animals in Group 3 by intraperitoneal injection every other day. 2 mg/kg Everolimus and 75 mg/kg ABT-737 were intraperitoneally injected to the animals in Group 4 every other day starting on day 4 following the tumor implantation. At the end of 11 injections, which were performed every other day, the experiment was terminated by sacrification of the animals. The tumors that developed in the animals were photographed, isolated, weighed, and sent for pathological examination. The organs (brain, thymus, heart, lung, stomach, liver, spleen, intestine, kidney and testis) that were taken from the animals were also sent for pathological examination to determine the toxic effect of the drugs.

Statistical Analysis

The results obtained were statistically evaluated by multiple t test analysis using GraphPad Prism 7 software, and $p<0.05$ was considered significant. (*$P\leq0.05$;  $P\leq0.01$; * $P\leq0.001$; **** $P\leq0,0001$). For example, when 0.05 p value denotes 5% significance level, it indicates 95% confidence and 5% margin of error.

Experimental Results

Figure 3A:
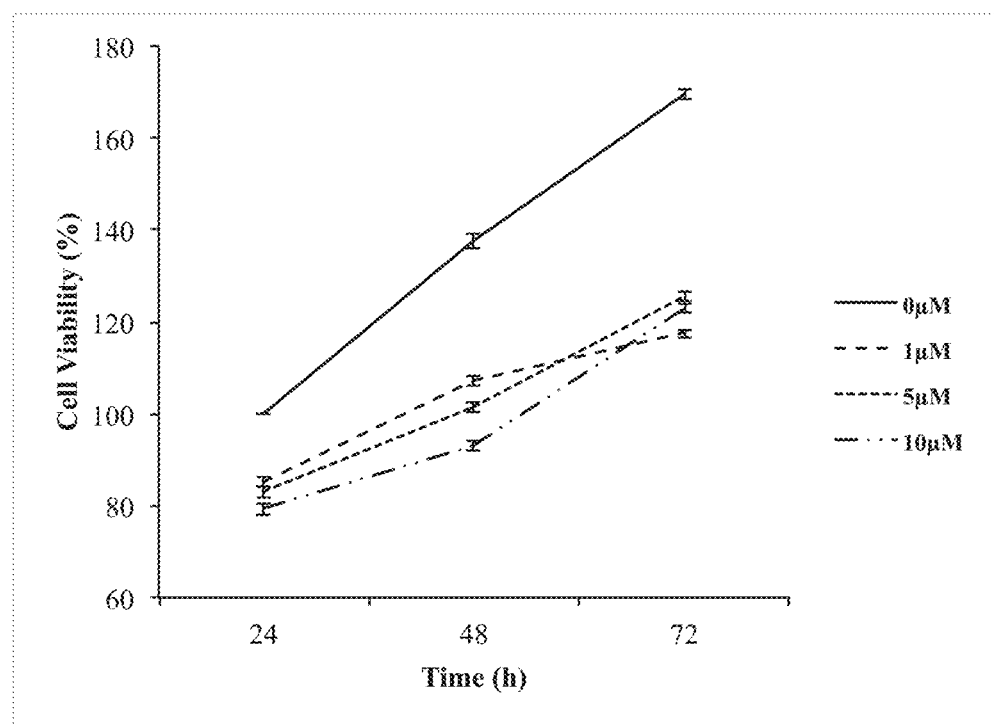
FIG. 3A shows the toxic effect of Everolimus monotherapy on A-498 cells.
Figure 3B:
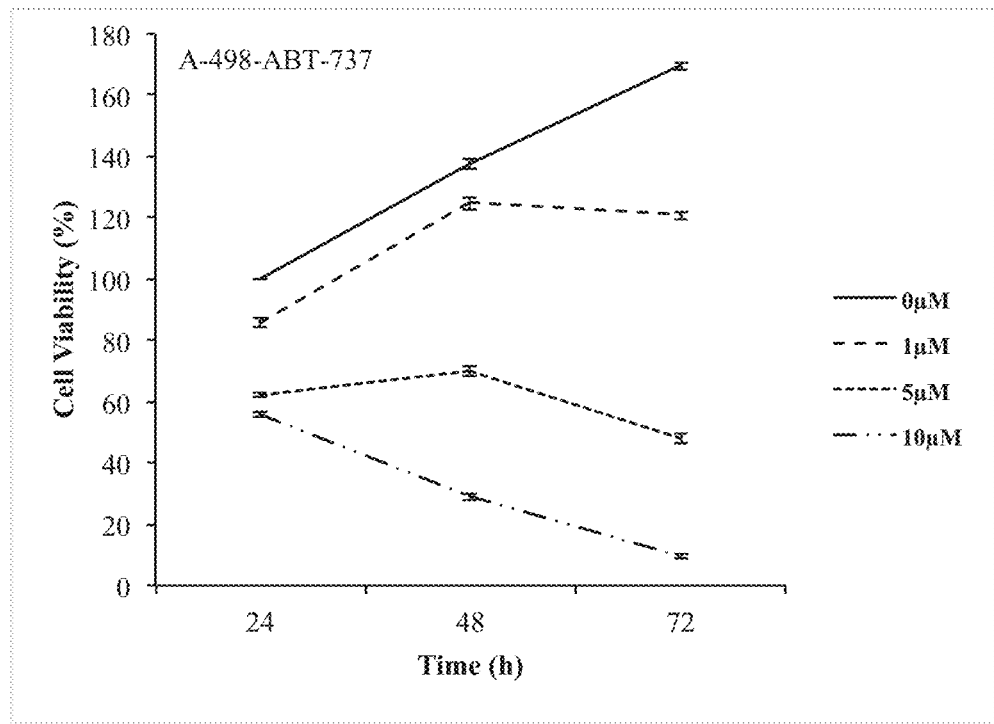
FIG. 3B shows the toxic effect of ABT-737 monotherapy on A-498 cells.

Everolimus-resistant primary A-498 and metastatic Caki-1 renal cell carcinoma (RCC) cell lines were used in WST-1 cell viability assays to determine the effect of the drug composition, the scope of the present invention, on cell viability. According to our results, concentrations of 1 μM Everolimus and 5 μM ABT-737 were decided as the drug composition to be administered to the A-498 cells (FIG. 3).

Figure 4A:
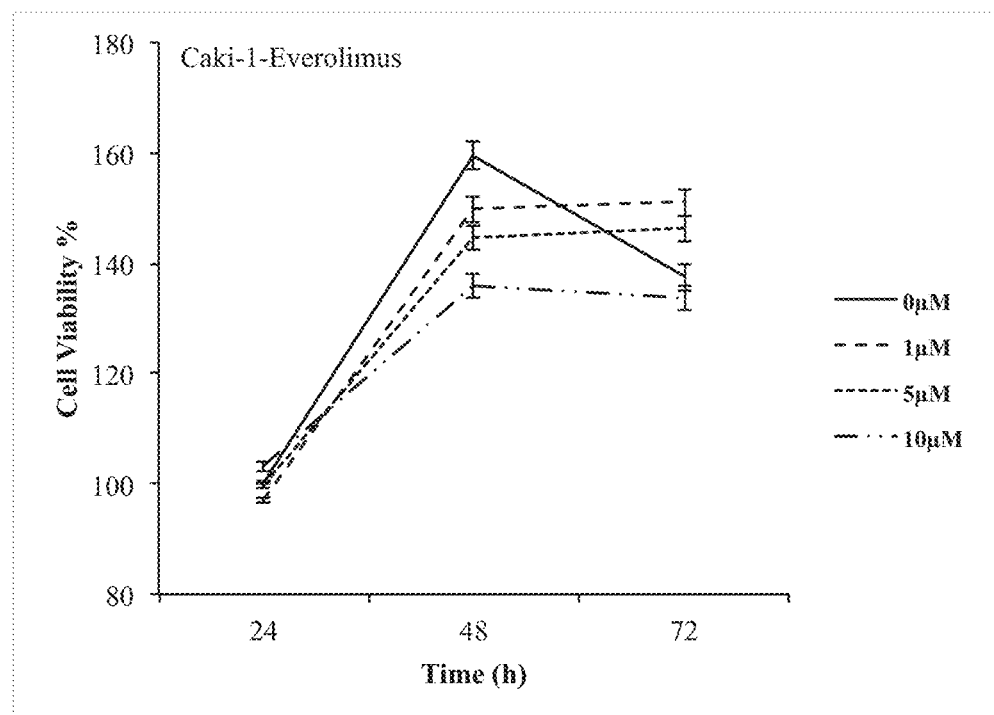
FIG. 4A shows the toxic effect of Everolimus monotherapy on Caki-1 cells.
Figure 4B:
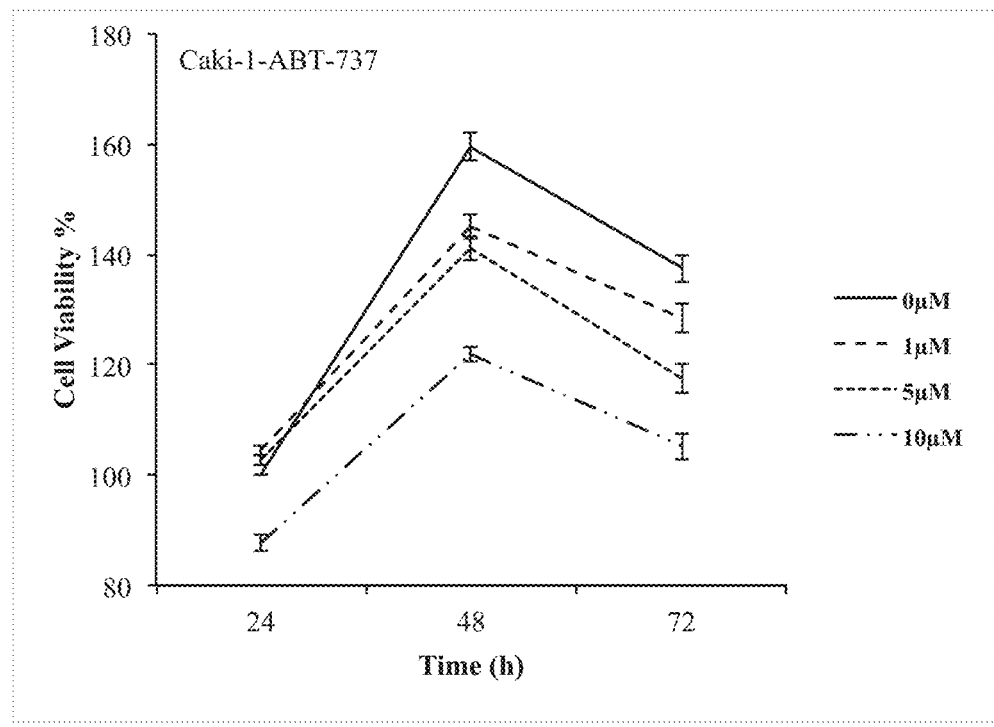
FIG. 4B shows the toxic effect of ABT-737 monotherapy on Caki-1 cells.

Similarly, Caki-1 cells were decided to be treated with the drug composition containing 1 μM Everolimus and 10 μM ABT-737 (FIG. 4).

In agreement with the literature, the analysis of our toxicology results showed that A-498 (FIGS. 3A and 3B) and Caki-1 (FIGS. 4A and 4B) cells were resistant to Everolimus.

Figure 5:
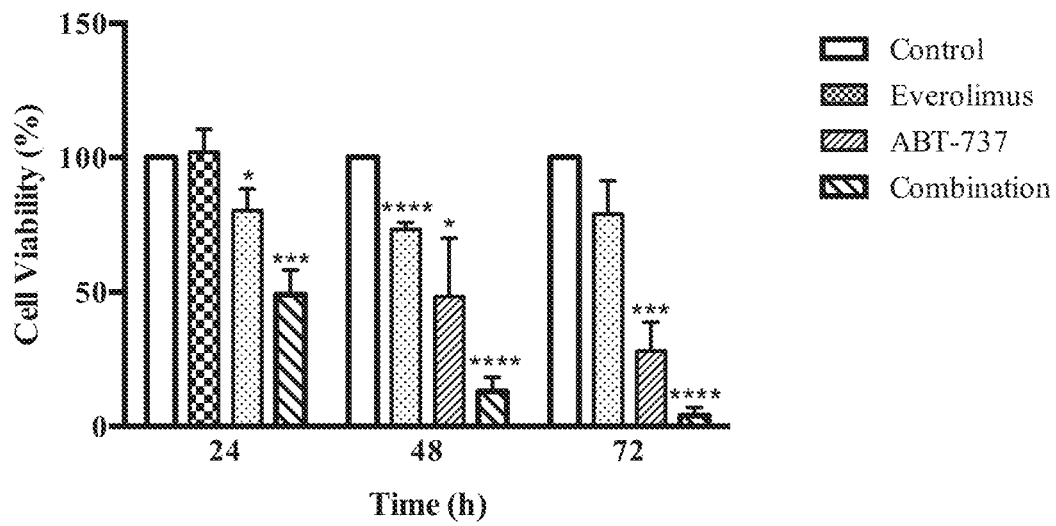
FIG. 5 demonstrates of the toxic effect of the drug composition on A-498 cells (*$P \leq 0.05$;  $P \leq 0.01$; * $P \leq 0.001$; **** $P \leq 0.0001$). The P value represents a statistical evaluation of the probability of the occurrence of a result.
Figure 6:
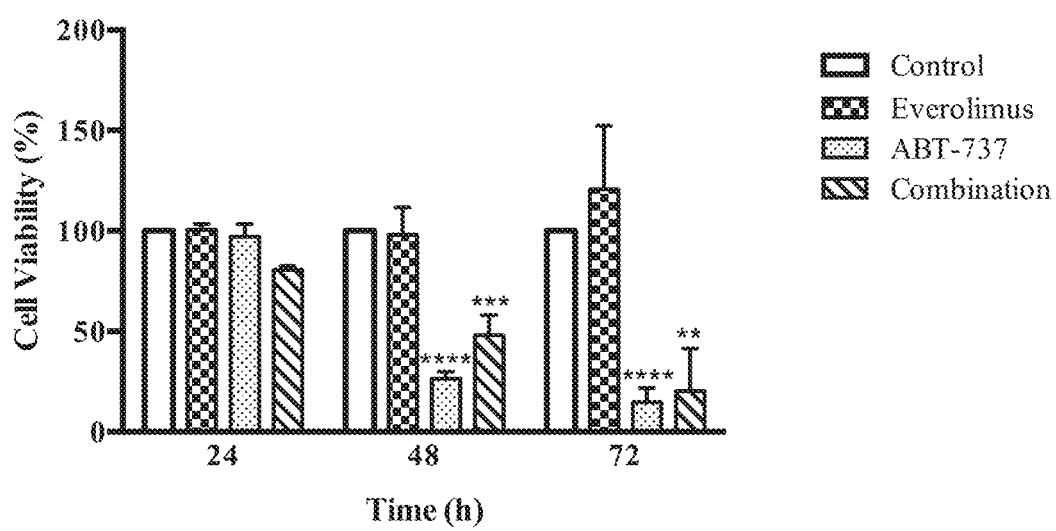
FIG. 6 Determination of the effect of the drug composition on Caki-1 cell viability (*$P \leq 0.05$;  $P \leq 0.01$; * $P \leq 0.001$; **** $P \leq 0.0001$). For example, when a p value of 0.05 denotes 5% significance level, it indicates 95% confidence and 5% margin of error.

When Everolimus and ABT-737 were administered together, toxic effects were observed in both cell lines beginning from the second day of treatment (FIGS. 5 and 6). After three days of analysis, the drug composition reduced the viability in A-498 cells about 90% more in comparison to the monotherapy with ABT-737 (FIG. 5). ABT-737 monotherapy was successful in Caki-1 cells, where an 80% decrease in cell viability was observed after 72 hours. The drug composition reduced the viability of Caki-1 cells about 60% more compared to the cells in the control group (non-treated) and cells treated with Everolimus (FIG. 6).

Figure 7A:
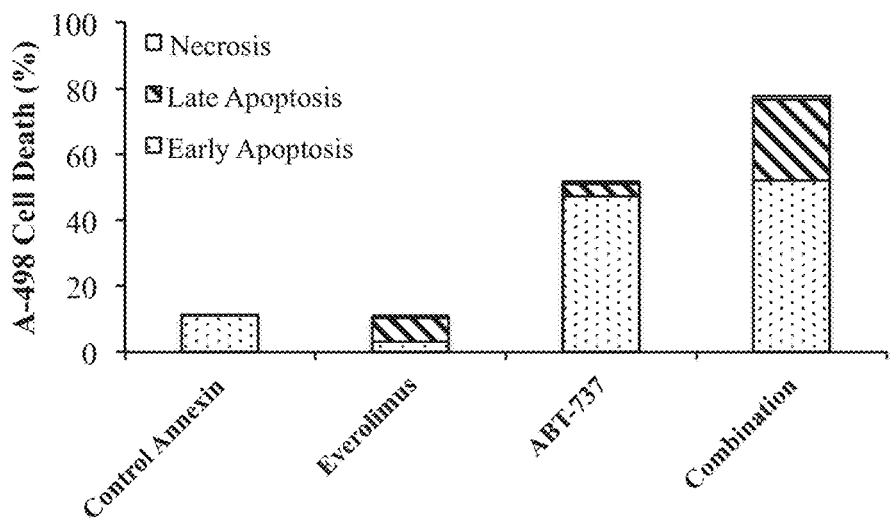
FIGS. 7A-7C demonstrate the effect of the drug composition on apoptosis mediated cell death in A-498 cells in a: 24 hours, b: 48 hours, and c: 72 hours respectively.
Figure 7B:
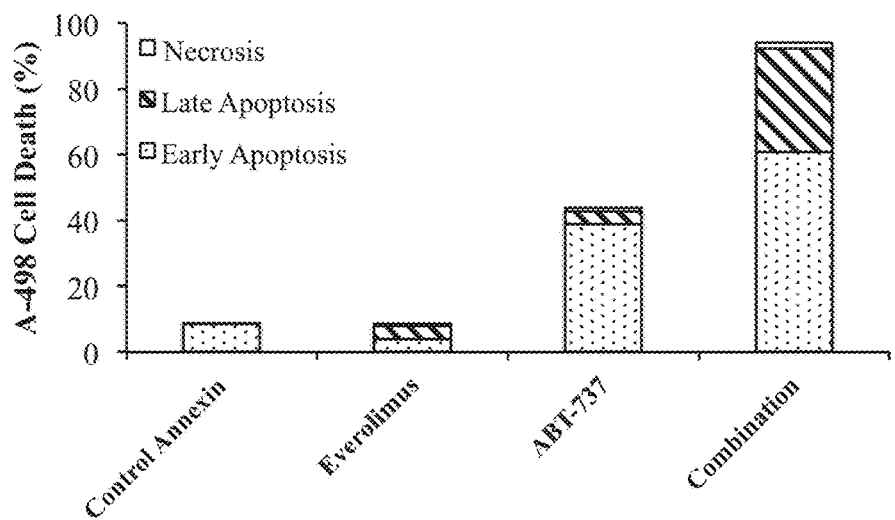
Figure 7C:
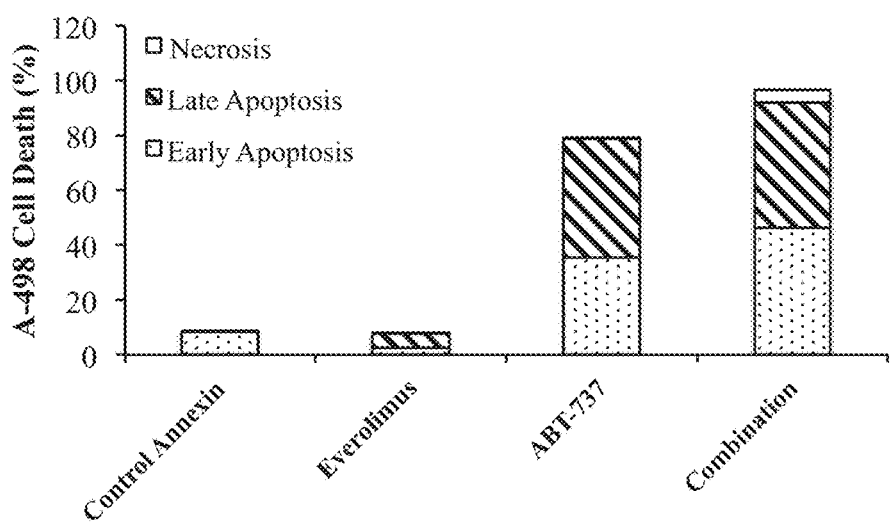

The Annexin-V method was used to determine whether the decrease in the cell viability caused by the drug composition is the result of cell death. Early apoptosis was observed at the end of 24 hours in A-498 cells which were cotreated with 1 µM Everolimus and 5 µM ABT-737 (FIG. 7A). At the end of 48 and 72 hours, significant cell death was observed in the cells including early and late apoptosis (FIGS. 7B and 7C).

Figure 8A:
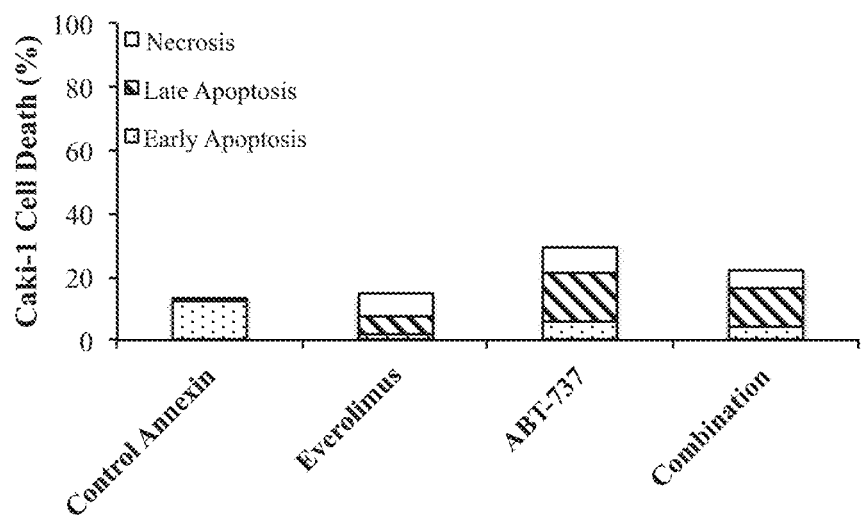
FIGS. 8A-8C show the effect of the drug composition on apoptosis mediated cell death in Caki-1 cells in a: 24 hours, b: 48 hours, and c: 72 hours respectively.
Figure 8B:
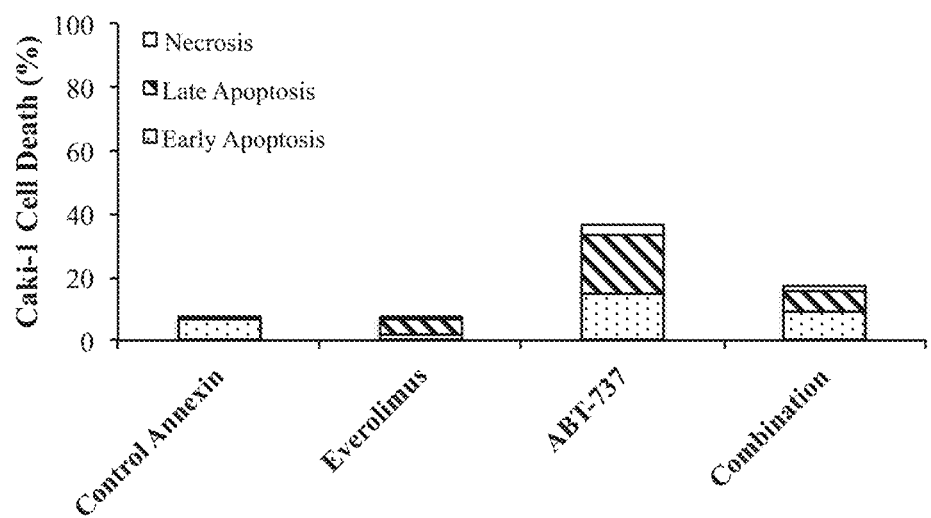
Figure 8C:
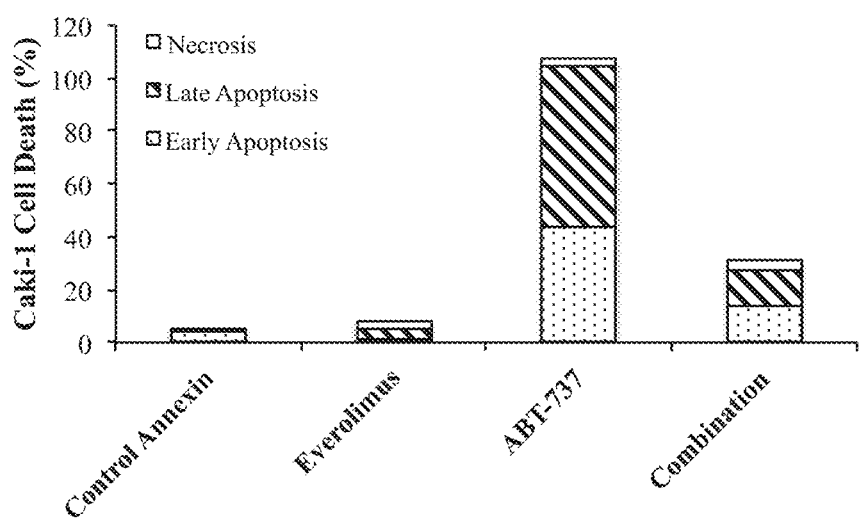

The monotherapy of ABT-737 led to a more significant increase in the cell death compared to the combination that caused to cell death in metastatic Caki-1 cells treated with 1 µM Everolimus and 10 µM ABT-737 after 24, 48 and 72 hours of treatment, (FIGS. 8A, 8B and 8C). This analysis revealed that the drug composition led to apoptosis-induced cell death in both RCC cell lines and ABT-737 monotherapy could also provide successful outcome in metastatic RCC treatment.

The expressions of caspase proteins involved in the apoptosis pathway were examined by Western Blotting technique in order to understand the molecular mechanism of cell death observed as a result of the drug composition. Cytochrome c, which is released into the cytoplasm during cell death through the channel formed by the pro-apoptotic Bax/Bak proteins in the mitochondrial membrane, forms a complex called "apoptosome" together with the other cell death proteins APAF1 (apoptotic protease activating factor 1) and pro-caspase 9, and thereby activates pro-caspase 9. The active caspase 9 activates the executioner caspases (pro-caspases 3, 6, 7) and induces apoptosis [36, 37]. For this reason, the breakdown in caspase proteins is associated with the activation of the apoptosis mechanism. The drug composition caused to cleavage of caspase 3 and caspase 9 proteins in the protein lysates isolated from A-498 and Caki-1 cells that were treated for 24 hours with the above-mentioned drug doses. These results validated the cell death inducing effect of the drug composition in both cell lines in a molecular aspect (FIGS. 9A and 9B).

Another molecular mechanism affected by Everolimus and ABT-737 combination is the PI3K/AKT/mTOR survival pathway. This pathway is induced by the growth factors and plays a central role in important cellular processes such as the cell growth, proliferation, migration, survival and angiogenesis [4, 5]. Everolimus, used in our study, only inhibits mTOR kinase in the mTORC1 complex by binding to the 12 kilodalton FK506 binding protein FKBP12 [9]. A-498 RCC cells were treated with 1 µM Everolimus and 5 µM ABT-737, while Caki-1 cells were treated with 1 µM Everolimus and 10 µM ABT-737 for 24 hours. After 24 hours, the protein lysates were isolated from the cells. The expression levels of proteins playing a role in mTOR pathway were analyzed by Western Blotting technique to investigate the effect of the drug composition on the mTOR pathway.

Upon induction by the growth factors, the phosphorylated AKT at threonine 308 (AKT-T308P) is activated, which in turn activates the mTOR kinase in the mTORC1 complex. The activated mTOR kinase undergoes autophosphorylation at serine 2448 (mTOR-S2448P) [38]. Therefore, an increase observed in the expression of the phosphorylated derivative of mTOR kinase at serine 2448 indicates the active mTORC1 pathway. The mTOR kinase, which is activated in the mTOR pathway signaling mechanism, phosphorylates the p70S6K protein, one of its target proteins, at threonine 389 (p70S6K-T389P) [39]. Thus, the activated p70S6 kinase enables the initiation of the protein translation by phosphorylating its target protein ribosomal S6 at serine 5240/244 (S6-S240/244P) site [40].

Figure 11:
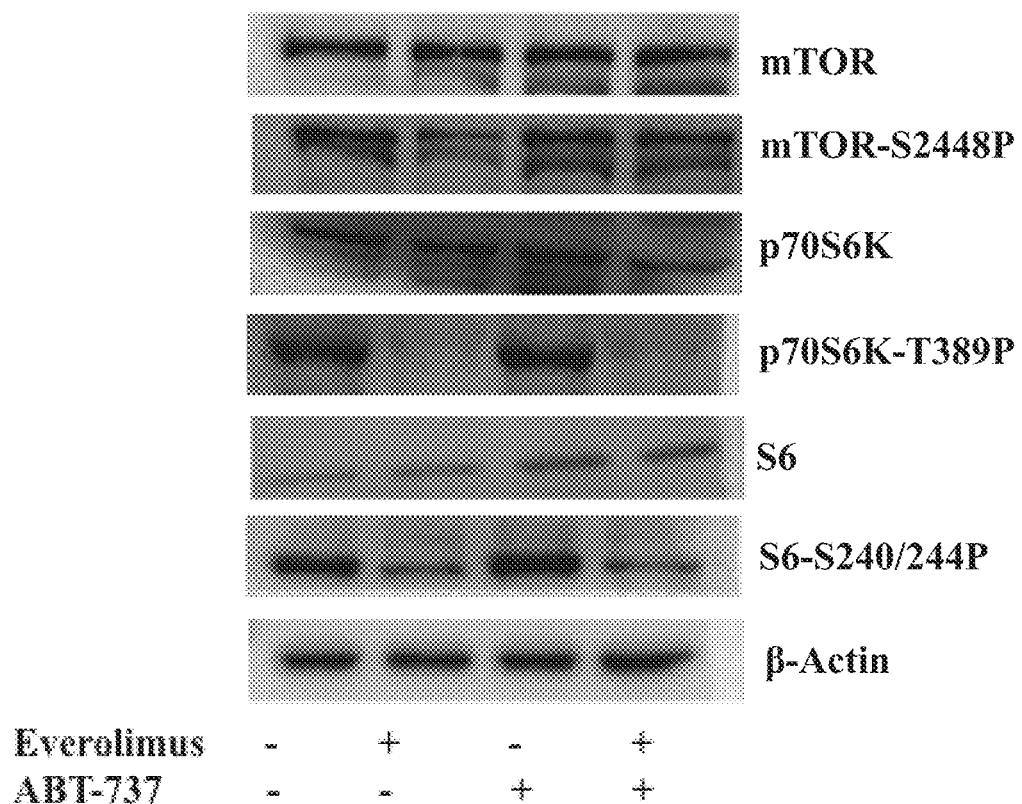
FIG. 11 shows the of the effect of the drug composition on mTOR pathway for Caki-1 cells. mTOR: Mammalian target of rapamycin; mTOR-S2448P: phosphorylated derivate of Mammalian target of rapamycin at serine 2448 site; p70S6K: Ribosomal protein S6 kinase; p70S6K-T389P: phosphorylated derivate of Ribosomal protein S6 kinase in threonin 389 region; S6: Ribosomal protein S6; S6-S240/244P: phosphorylated derivate of Ribosomal protein S6 at serine 240/244 site. Cytoskeleton protein β-Actin was used to show equal loading.

It was observed that 1 µM Everolimus and the drug composition diminished the autophosphorylation of the mTOR kinase at serine 2448 in both A-498 (FIG. 10) and Caki-1 (FIG. 11) cells compared to the untreated control cells. It was determined that, in addition to the Everolimus treatment, the combination of Everolimus and ABT-737 decreased the basal p70S6K protein expression compared to the control cells, and this decrease was also observed in the derivative of p70S6K protein phosphorylated at threonine 389. While the expression of the S6 protein, the target protein of the p70S6 kinase, decreased in A-498 cells (FIG. 10) as a result of the drug treatments, the treatments caused an increase in Caki-1 cells (FIG. 11). In both cell lines, a decrease was observed in the expression of the phosphorylated active derivative of the same protein at serine 240/244 upon Everolimus treatment. A significant decrease in the derivative of the S6 protein at serine 240/244 was observed after Everolimus and ABT-737 drug composition. These findings of the experiment performed on A-498 and Caki-1 cells showed that Everolimus and ABT-737 drug composition suppressed the mTOR pathway.

According to results of in vitro experiments, it was determined that Everolimus and ABT-737 drug composition induced to cell death in the A-498 and Caki-1 cell lines. Based on these findings, in vivo studies were performed to observe the clinical effect of the drug composition. RenCa (murine renal adenocarcinoma) cells, widely used in the literature, were used to generate a kidney cancer model in animals. Hrushesky and Murphy were first developed the RenCa cell model in the 1970s by isolating cells from the kidney tumors that spontaneously grow from the kidneys of the balb-c mice [31].

Figure 12:
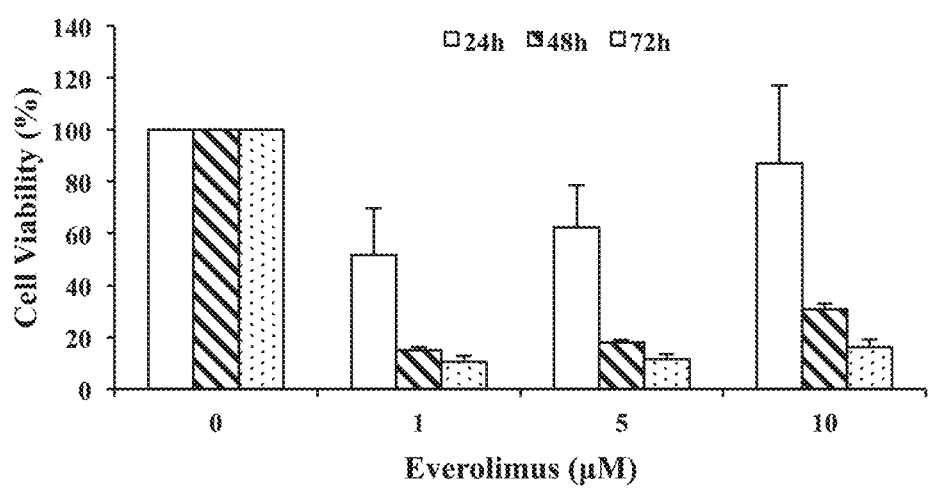
FIG. 12 is the representation of the toxic effect of Everolimus on RenCa cells.
Figure 13:
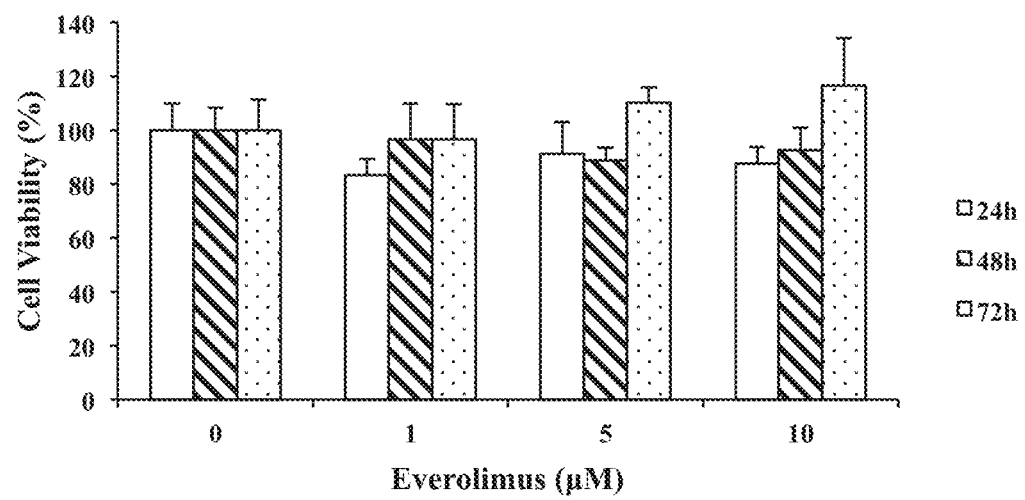
FIG. 13 is the representation of the Everolimus resistance developed in RenCa cells.

Before starting the in vivo experiments with RenCa cells, the effect of the drug Everolimus on the viability of these cells was investigated by the WST-1 method. Everolimus (1, 5 and 10 µM) prepared at different concentrations caused toxic effects on RenCa cells after 48 hours of treatment (FIG. 12). These experiments showed that wild type RenCa cells can not give rise to Everolimus resistant kidney tumor that develops in humans. In order to overcome this problem, an Everolimus-resistant RenCa cell line was required to be developed. Therefore, Everolimus sensitive RenCa cells were first made resistant to Everolimus before starting the in vivo studies. FIG. 13 shows that Everolimus (1, 5 and 10 µM) prepared at different concentrations did not cause any change in the Everolimus-resistant RenCa (erRenCa) cell viability at the end of three days.

Figure 14:
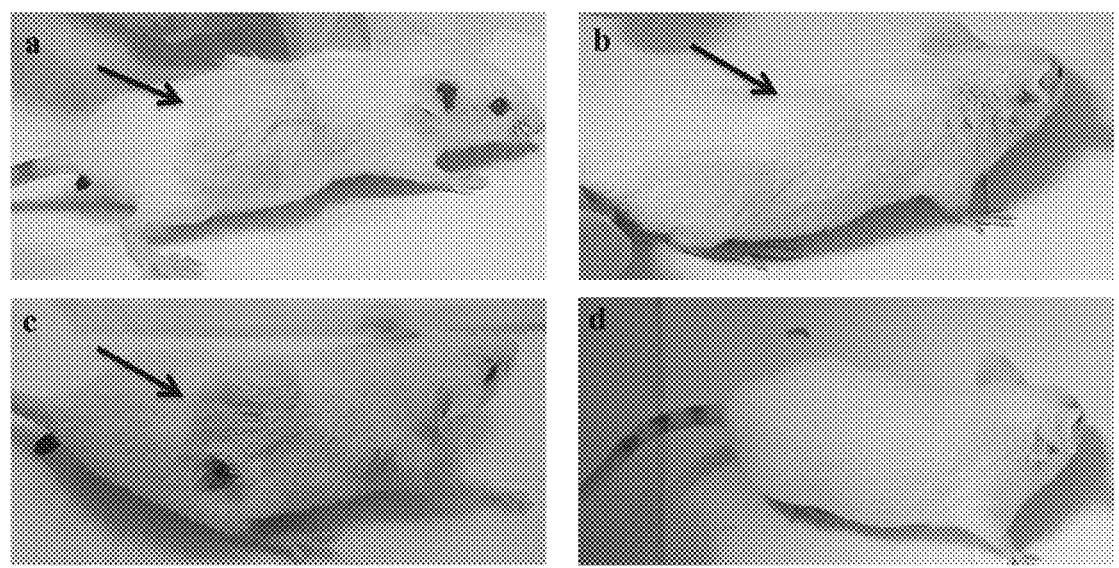
FIGS. 14A-14D show the representation of the tumors developed on the dorsal area of the animals by the injection of Everolimus-resistant RenCa (erRenCa) cells of a: Control group; b: Everolimus group; c: ABT-737 group; and d: ABT-737 and Everolimus combination group respectively.
Figure 15:
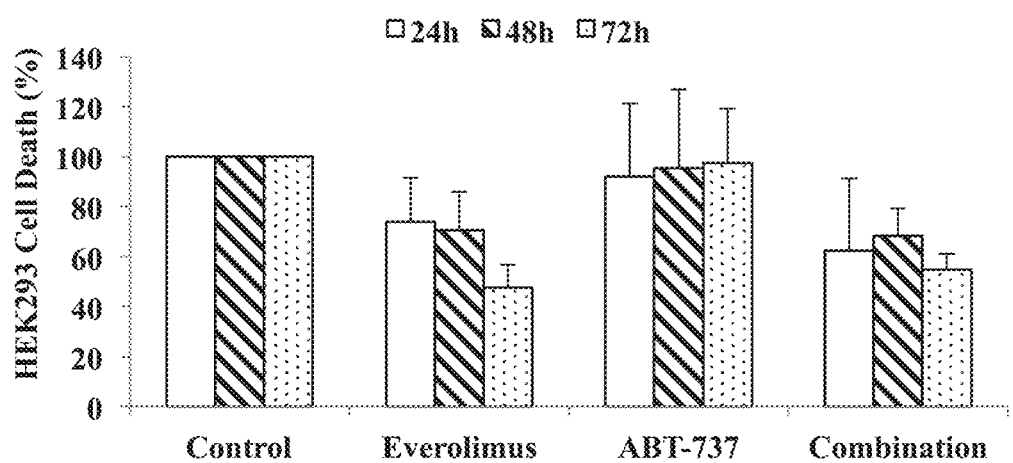
FIG. 15 is the representation of the toxic effect of the drug composition on HEK293 cells.

These erRenCa kidney cancer cells were used as a cancer cell line to form a kidney cancer tumor model in animals. For this purpose, cells were subcutaneously injected into the dorsal area of Balb/c mice. At the end of the fourth day following the injection, 2 mg/kg Everolimus and 75 mg/kg ABT-737 drug composition was intraperitoneally administered to the animals every other day. The experiment was terminated at the end of 11 injections. Tumor formation was observed in eight animals in the control group, which were not subjected to the drug treatments (FIG. 14A). In comparison to the control animals, tumor formation was observed in four of the eight animals treated only with Everolimus (FIG. 14B). The tumor formation was detected in three of the eight animals treated only with ABT-737 (FIG. 14C). The tumor formation was not observed in any of the eight animals in the combination group treated with the drug composition (FIG. 14D). In order to develop resistance to Everolimus, erRenCa cells inactivated their mTOR pathway and began to use the Bcl-2 pathway for their survival. Therefore, cancer cells could only undergo cell death after blocking the anti-apoptotic Bcl-2 survival pathway with the drug ABT-737.

At the end of the experiment, the organs including thymus, heart, stomach, intestine, kidney, spleen, testis, lung, liver, and brain were taken from the animals in each group and were sent for pathological examination. The pathological examination was performed to determine whether the drug treatment caused any toxic effects on the isolated tissues. At the same time, the metastatic focus in these tissues was also examined. Pathological analysis revealed no toxic effect in the above-mentioned organs.

Pathologic examination of the tumor tissue formed in the animals revealed that these tumors were renal cell carcinomas. Tissue deaths, which are called necrosis, have been detected in the tumors that developed in animals (Tables 1, 2, 3 and 4). Necrosis in cancer tissue is triggered by the pathological events (such as infection, cancer or inflammation) and occurs in the tumor particularly, when vascular support is insufficient. Accordingly, necrosis is a form of cell death that results from the chemical and structural disruption of the cell integrity. A four-score grading system has been advised by WHO/ISUP (World Health Organization/International Society of Urological Pathology) for renal cell carcinoma. Tumors are graded with a score of 1 to 3 according to their nucleolar appearance. Grade four is determined depending on the presence of the significant nuclear pleomorphism (variability of a cell in several different shapes), tumor giant cells, and/or sarcomatoid (resembling malignant tumor arising in connective tissue) differentiation. In this context, while tumors of grade 4, which is the highest grade, were observed in the untreated animals, the tumors formed in mice receiving Everolimus and ABT-737 monotherapy were found to be at different grades. Furthermore, no metastatic tumor finding was observed in the animals' organs including as thymus, heart, stomach, intestine, kidney, spleen, testis, lung, liver and brain.

TABLE 1

Results of the pathological examination of the tumors isolated from the animals of control group.

| Control | Tumor | Grade | Necrosis |
|---|---|---|---|
| H1 | Renal cell carcinoma | 4 | Yes |
| H2 | Renal cell carcinoma | 4 | Yes |
| H3 | Renal cell carcinoma | 4 | Yes |
| H4 | Renal cell carcinoma | 4 | Yes |
| H5 | Renal cell carcinoma | 4 | Yes |
| H6 | Renal cell carcinoma | 4 | Yes |
| H7 | Renal cell carcinoma | 4 | Yes |
| H8 | Renal cell carcinoma | 4 | Yes |

TABLE 2

Results of the pathological examination of the tumors isolated from the animals of Everolimus group.

| Everolimus | Tumor | Grade | Necrosis |
|---|---|---|---|
| H1 | Renal cell carcinoma | 4 | Yes |
| H2 | No tumor | — | No |
| H3 | No tumor | — | No |
| H4 | No tumor | — | No |
| H5 | Renal cell carcinoma | 4 | No |
| H6 | Renal cell carcinoma | 2 | No |
| H7 | No tumor | — | No |
| H8 | Renal cell carcinoma | 4 | No |

TABLE 3

Results of the pathological examination of the tumors isolated from the animals of ABT-737 group.

| ABT-737 | Tumor | Grade | Necrosis |
|---|---|---|---|
| H1 | Renal cell carcinoma | 4 | No |
| H2 | Renal cell carcinoma | 4 | No |
| H3 | No tumor | — | No |
| H4 | No tumor | — | No |
| H5 | No tumor | — | No |
| H6 | No tumor | — | No |
| H7 | No tumor | — | No |
| H8 | Renal cell carcinoma | 4 | No |

TABLE 4

Results of pathological examination of the tumors taken from the animals of combination group.

| Combination | Tumor | Grade | Necrosis |
|---|---|---|---|
| H1 | No tumor | — | No |
| H2 | No tumor | — | No |
| H3 | No tumor | — | No |
| H4 | No tumor | — | No |
| H5 | No tumor | — | No |
| H6 | No tumor | — | No |
| H7 | No tumor | — | No |
| H8 | No tumor | — | No |

In addition to the results of the above-mentioned experiment, healthy human embryonic kidney (HEK293) cells were used in the cell viability assay to determine whether the drug composition causes any toxic effect. 1 µM Everolimus agent applied to the HEK293 cells for 24 and 48 hours did not show any cytotoxic effect, while the 72 hour-treatment led to a 50% decrease in the cell viability when compared to untreated control cells. In comparison to Everolimus agent, ABT-737 did not affect the viability in healthy kidney cells. In fact, even on the third day of the treatment, 5 µM ABT-737 agent did not cause any decrease in the cell viability and the cells continued to proliferate. In addition to the monotherapies, no significant decrease was observed in the cell viability when cells were treated with the drug composition for 24, 48 and 72 hours.

The invention shows that Everolimus and ABT-737 drug composition can be used for the treatment of renal cell carcinoma.

Application of the Invention

Within the scope of the invention, Everolimus, which is a targeted drug, was used in combination with the Bcl-2 inhibitor ABT-737 to improve the survival potential in patients with RCC that develop rapalog resistance and to develop a novel treatment strategy for RCC.

In the light of the results presented above, it was seen that ABT-737 led to the cell death in RCC cell lines when used alone or in combination with Everolimus.

Additionally, the inhibition of tumor formation in animals which received ABT-737 monotherapy and Everolimus-ABT-737 combination suggests that this drug may provide a therapeutic potential for RCC treatment. In this regard, it is requested that the administration of Navitoclax (ABT-263), an orally available analog of ABT-737, and other Bcl-2 inhibitors alone or in combination with Everolimus, which is administered once a day at a dose of 10 mg, to be patented for use in the treatment of rapalog-resistant RCC.

Renal cell carcinoma (RCC), which accounts for 2-3% of the malignant tumors in adults, is the most common malignant tumor (85%) among kidney cancer types and has a mortality rate of 50%. The VHL mutation detected in 90% of RCC tumors causes activation of the HIF-α transcription factors, which in turn activate the PI3K-AKT-mTOR survival pathway resulting in intense vascularization and metastasis of the tumors. Everolimus, one of the drugs currently used in the treatment of metastatic RCC, targets this kinase pathway thereby inhibiting cell growth/survival. However, chemotherapeutic treatments with these drugs can only prolong the life spans of patients diagnosed with advanced stage or metastatic RCC, but they cannot treat the disease and reduce the mortality rate. One of the reasons for the failure to reach the desired success in the treatment of metastatic RCC is the resistance of the tumors against the chemotherapeutic treatment. In the literature, chemotherapeutic drug resistance observed in RCC is associated with the high expression of the anti-apoptotic Bcl-2 protein. In this regard, the study, which is supported by the TUBITAK (114S332) and the subject matter of the present patent application, investigated the success of the combination therapy with the Bcl-2 anti-apoptotic inhibitor ABT-737 in the treatment of RCC tumors that develop resistance to drug Everolimus.

In this context, the effect of Everolimus and ABT-737 drug composition on cell survival and cell death were shown in Everolimus-resistant RCC cell lines exhibiting overexpression of Bcl-2 protein by in vitro and in vivo experiments. The mechanism by which the drug composition shows its effect on RCC was analyzed from a molecular point of view. There are no preclinical or in vitro studies wherein ABT-737 is used for the treatment of RCC. In this regard, it is requested that the administration of Navitoclax (ABT-263), an orally available analog of ABT-737, and other Bcl-2 inhibitors alone or in combination with Everolimus, which is administered once a day at a dose of 10 mg, to be patented for the use in the treatment of rapalog-resistant RCC.

The invention relates to a chemotherapeutic drug composition, which is produced by the combination of Bcl-2 anti-apoptotic inhibitor ABT-737 with mTOR inhibitor Everolimus against RCC tumors that have developed rapalog resistance and for the treatment of metastatic renal cell carcinoma (RCC), which comprises 2-3% of the malignant tumors nowadays. Within the scope of the invention, the success of the treatment with the present composition in the RCC treatment was investigated. In this regard, the effect of Everolimus and ABT-737 drug composition on cell survival and cell death in rapalog-resistant RCC cell lines with high expression of Bcl-2 protein was shown by in vitro and in vivo experiments and the mechanism of the effect of the drug composition on RCC was analyzed from a molecular point of view. The scope of the invention includes administering Navitoclax (ABT-263), an orally available analog of ABT-737 and other Bcl-2 inhibitors alone or in combination with Everolimus, which is administered once a day at a dose of 10 mg, for the use in the treatment of rapalog-resistant RCC.

What is claimed is:

1. A drug composition for treatment of kidney cancer, comprising a solution of ABT-737, and a final solution concentration of 75 mg/kg; and
    the drug composition further comprises an Everolimus solution, and a final concentration of the Everolimus solution is 2 mg/kg;
    wherein the kidney cancer is rapalog-resistant advanced kidney cancer.

2. A method of preparing the drug composition of claim 1, comprising the steps of
    preparing the solution with a concentration of 10 mM by dissolving 10 mg ABT-737 in 1.229 ml DMSO,
    for in vivo conditions, diluting the solution in PBS (Phosphate-buffered saline) to have a drug concentration of 75 mg/kg.

3. The method of claim 2, further comprising:
    preparing an Everolimus stock solution with a concentration of 10 mM by dissolving 10 mg lyophilized Everolimus in 1.043 ml DMSO (Dimethyl sulfoxide),
    for in vivo conditions, diluting a sample taken from Everolimus stock concentration in PBS (Phosphate-buffered saline) to have a drug concentration of 2 mg/kg.

* * * * *